United States Patent [19]
Mills

[11] Patent Number: 5,515,868
[45] Date of Patent: May 14, 1996

[54] SURGICAL DRAPE HAVING AT LEAST ONE OPENABLE AND RECLOSABLE SLIT FORMED THEREIN

[75] Inventor: Veronica A. Mills, Cincinnati, Ohio

[73] Assignee: Standard Textile Co., Inc., Cincinnati, Ohio

[21] Appl. No.: 270,464

[22] Filed: Jul. 5, 1994

[51] Int. Cl.⁶ .................................................. A61B 19/08
[52] U.S. Cl. ........................ 128/854; 128/853; 128/849
[58] Field of Search ........................... 128/849–856, 128/849–856

[56] References Cited

U.S. PATENT DOCUMENTS

| | | | |
|---|---|---|---|
| 3,750,664 | 8/1973 | Collins | 128/853 |
| 3,910,268 | 10/1975 | Miller | 128/854 |
| 3,926,185 | 12/1975 | Krzewinski | 128/854 |
| 3,930,497 | 1/1976 | Krebs et al. | 128/853 |
| 4,027,665 | 6/1977 | Scrivens . | |
| 4,041,942 | 8/1977 | Dougan et al. . | |
| 4,334,529 | 6/1982 | Wirth . | |
| 4,479,492 | 10/1984 | Singer | 128/853 |
| 4,561,434 | 12/1985 | Taylor | 128/849 |
| 4,627,426 | 12/1986 | Wegener et al. | 128/849 |
| 4,664,103 | 5/1987 | Martin et al. | 128/852 |
| 4,957,120 | 9/1990 | Grier-Idris | 128/849 |
| 5,109,873 | 5/1992 | Marshall | 128/849 |
| 5,125,995 | 6/1992 | D'Haese . | |
| 5,341,821 | 8/1994 | DeHart | 128/849 |

FOREIGN PATENT DOCUMENTS

| | | | |
|---|---|---|---|
| 1187363 | 5/1958 | Canada | 128/855 |

*Primary Examiner*—Jessica J. Harrison
*Assistant Examiner*—Michael O'Neill
*Attorney, Agent, or Firm*—Frost & Jacobs

[57] ABSTRACT

A reusable fabric surgical drape such as a cardiovascular drape, for example, having a fenestration to be positioned at a surgical site and one or more slits formed in the drape. Each slit has overlapping edges which are releasably attachable together. The surgical drape may have one such slit extending from the fenestration to an edge of the drape, which, when opened, enables removal of the drape from the patient about any surgical equipment attached to the patient through the fenestration. One or more additional such slits may be formed in the drape and so positioned and shaped as to provide, when opened, reclosable surgical site fenestrations.

9 Claims, 2 Drawing Sheets

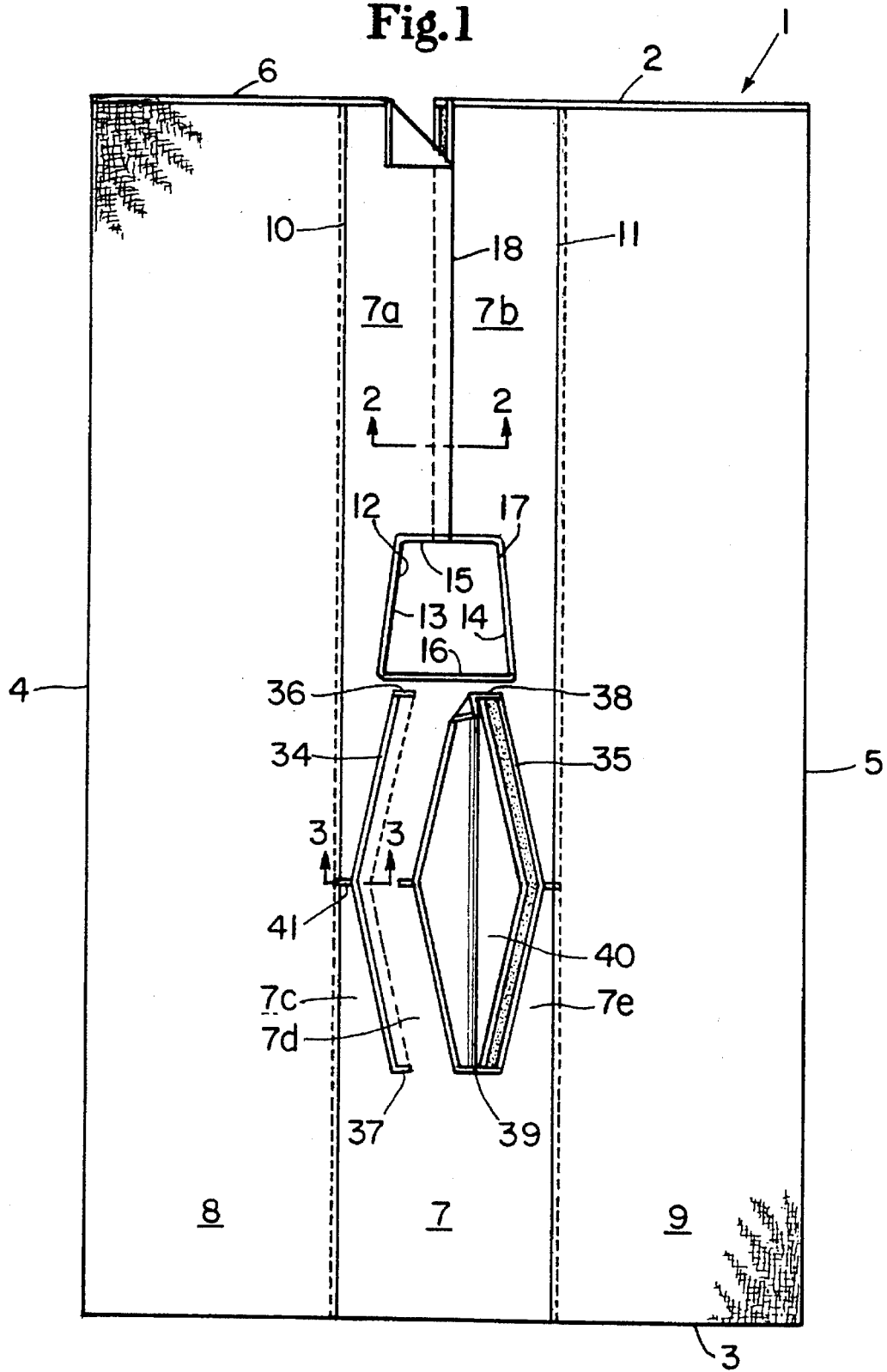

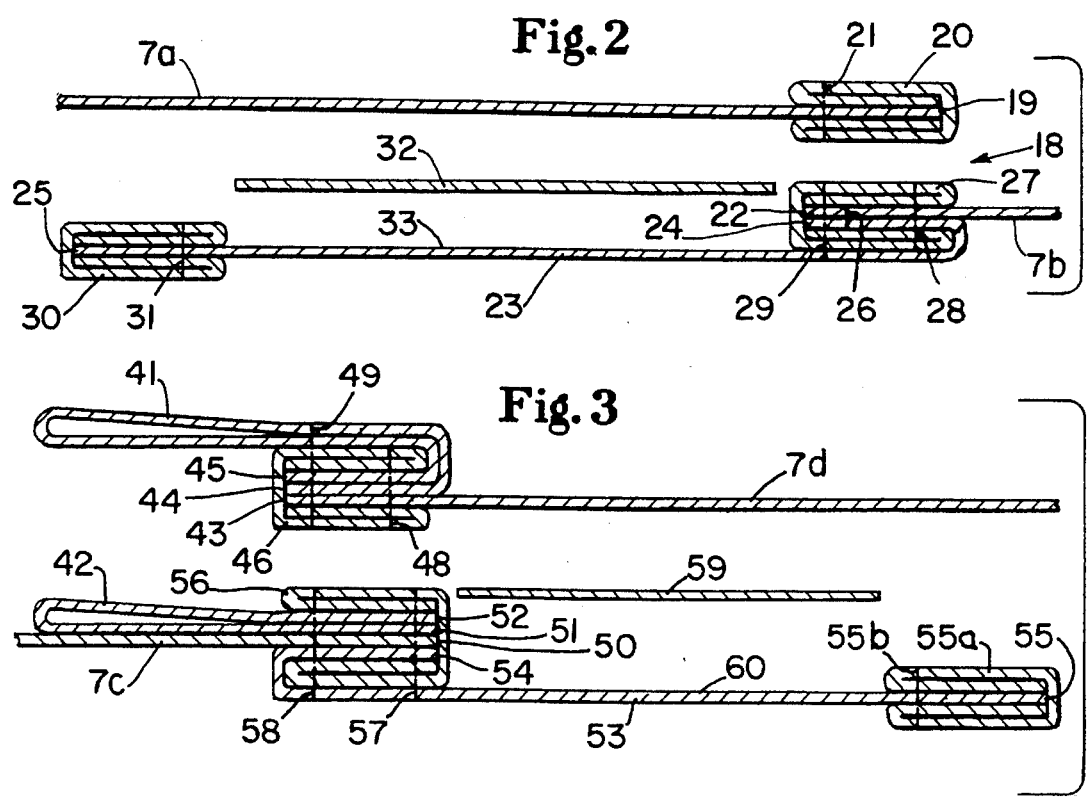

SURGICAL DRAPE HAVING AT LEAST ONE OPENABLE AND RECLOSABLE SLIT FORMED THEREIN

TECHNICAL FIELD

The invention relates to a reusable surgical drape having an openable and reclosable slit from an operating site fenestration to an edge of the drape for removal of the drape without disconnection of tubes and the like connected to the patient's body at the operation site and having additional reclosable slits defining reclosable fenestrations.

BACKGROUND ART

While the teachings of the present invention are applicable to many types of surgical drapes, for purposes of an exemplary showing, they will be described in their application to a reusable cardiovascular surgical drape.

It is the usual practice to provide a cardiovascular surgical drape with a rather large fenestration exposing the patient's chest. A number of surgical procedures involving the heart require the attachment to the patient's chest of tubes, wires or the like which are connected to various medical devices, all as is well known in the art. Since these tubes, wires or the like are applied to the patient's chest area during the operation and through the surgical drape fenestration, a problem arises when the procedure is ended and it is desired to remove the surgical drape. When a disposable surgical drape is used, a usual procedure is to simply cut a slit in the surgical drape from the fenestration to one of the drape edges, enabling the drape to be pulled about the tubes and wires and removed from the patient.

From a similar standpoint, the use of a reusable cardiovascular surgical drape has disadvantages. Sometimes, the piece of equipment to which a wire or tube is attached is of such size that it will pass through the fenestration. Other equipment, however, will not. In such an instance, removal of the reusable surgical drape requires momentary disconnection of certain tubes and wires from their respective pieces of equipment, until the drape can be removed, after which the tubes and wires reconnected. Such disconnection and reconnection of tubes and wires may subject the operating room personnel to some risk of exposure to possible infectious fluids and may create some problems of maintaining sterility. Their have been instances where the removal problem for a reusable cardiovascular drape has been such that the surgeon has elected to cut the drape, much as would be done with a disposable drape. This, of course, effectively precludes reuse of the drape.

In some surgical procedures such as a by-pass procedure, veins are removed from at least one of the patient's legs to provide the by-pass material. When a disposable drape is used, it is common procedure for the surgeon to cut a fenestration in the disposable drape along the patient's leg involved. If both legs are involved, the surgeon will cut two fenestrations. Once the surgical procedure with respect to one or both legs is completed, the surgeon-made fenestration or fenestrations are closed through the use of an auxiliary drape device.

When a reusable surgical drape is employed, such a drape will normally be provided with an elongated, rectilinear fenestration for each leg. When one or both of these elongated rectilinear fenestrations are not being used, sterility is maintained by covering them with an auxiliary drape member.

The present invention is based upon the discovery that the above-noted problems, encountered with prior art cardiovascular surgical drapes, can be overcome through the provision of appropriately located slits formed in the drape and having overlapping material edges. The overlapping edges are provided with means to releasably join them together. One such slit extends from the chest fenestration to an edge of the surgical drape. This strip being openable to release the drape from the patient around any chest tubes or the like without disconnection thereof. The drape is additionally provided with a similar pair of slits at the location of each of the patient's legs, each of these slits being so shaped that, when opened, it will form an appropriate fenestration along its respective patient leg. Means are provided between the overlapping edges of each of these leg slits to maintain the leg slits closed when not being used, and therefore, making unnecessary the use of additional drape devices to maintain sterility.

DISCLOSURE OF THE INVENTION

According to the invention them is provided a reusable surgical drape having one or more slits formed therein. Each slit has overlapping material edges with means therebetween to releasably close the slit when not in use. One such slit may be provided and so located with respect to the surgical drape that it permits removal of the drape about equipment attached to the patient at the surgical site and through the drape fenestration. One or more of such slits may be positioned and shaped to form an openable and reclosable drape fenestration.

In a specific embodiment, the surgical drape is a cardiovascular surgical drape provided with a large fenestration exposing the patient's chest at the surgical site. A slit with overlapping edges extends from the chest fenestration to an edge of the drape, preferably the head end edge of the drape, to enable easy removal of the drape from the patient and about surgical equipment affixed to the patient's chest through the drape fenestration. The drape is additionally provided with a pair of slits with releasably closable overlapping edges, each slit of the pair being located along one of the patient's legs and providing reclosable fenestrations for surgical procedures performed on one or both of the patient's legs.

The releasably closable slits may employ a water dispersible, double-coated tape to accomplish the releasable closure. Other means may also be used, as will be set forth hereinafter.

BRIEF DESCRIPTION OF THE DRAWINGS

FIG. 1 is a simplified plan view of a cardiovascular drape embodying the teachings of the present invention,.

FIG. 2 is a fragmentary cross sectional view taken along section line 2—2 of FIG. 1.

FIG. 3 is a fragmentary cross sectional view taken along section line 3—3 of FIG. 1.

DETAILED DESCRIPTION OF THE INVENTION

In all of the Figures like parts have been given like index numerals. As indicated above, the teachings of the present invention will be set forth in their application to a cardiovascular surgical drape. It will be obvious to one skilled in the art, however, that the teachings of the present invention may be applied to other types of surgical drapes for procedures involving similar problems.

Reference is first made to FIG. 1 wherein a cardiovascular surgical drape is shown in somewhat simplified form and is generally indicated at 1. The drape 1 has a head end 2, a bottom end 3 and side edges 4 and 5. The drape 1 is reusable and is made of fabric. The drape is preferably hemmed along its bottom edge 3 and side edges 4 and 5. While not required, the head end 2 of drape 1 may be provided with a brightly colored binding tape 6. The brightly colored tape 6 clearly identifies the head end 2 of the drape and aids in folding and unfolding the drape.

The drape is made up of a central panel 7 and a pair of side panels 8 and 9, Preferably, the central panel 7 is made of a liquid repellant material, while the outer panels 8 and 9 are preferably made of a low liquid repellant fabric. The panels 7, 8 and 9 are joined together longitudinally along seams 10 and 11. The seams 10 and 11 are preferably double needle seams.

The central panel 7 is provided with a fenestration of such size and shape as to adequately expose the surgical site at the patient's chest. The fenestration 12 may have any appropriate peripheral configuration. In the particular embodiment illustrated, fenestration 12 is trapezoidal in configuration having a pair of side edges 13 and 14 and a head end edge 15 which is slightly shorter than the bottom end edge 16. Fenestration 12 is preferably provided with a peripherally extending binding tape 17 so as to assure that the edges 13–16 are smooth and finished.

In accordance with the teachings of the present invention, the drape 1 is provided with a longitudinal slit 18 which extends from the head end edge 15 of fenestration 12 through the head end edge 2 of the drape 1. The slit 18 essentially divides that portion of panel 7 between fenestration 12 and the head end edge 2 of the drape into two longitudinal halves indicated at 7a and 7b.

FIG. 2 is an exploded, fragmentary, cross sectional view taken along section 2—2 of FIG. 1. FIG. 2, for purposes of clarity, is diagrammatic in nature, the individual fabric and tape layers being greatly exaggerated in thickness. As will be apparent from FIG. 2, the panel half 7a terminates at slit 18 in a raw edge 19. The raw edge 19 is finished by a double fold bias tape 20 attached thereto by a straight stitch 21.

Along the slit 18, panel half 7b terminates in a raw edge 22. An additional web 23 has a first raw edge 24 and a second raw edge 25. The raw edge 22 of panel half 7b and the raw edge 24 of web 23 are joined together by a straight stitch 26. Raw edges 22 and 24 are finished by means of a double fold bias tape 27. The web 23 is brought about the adjacent portion of double fold bias tape 27 so as to constitute an extension of panel half 7b capable of being overlapped by panel half 7a. Panel half 7b, web 23 and double fold bias tape 27 are joined together by a pair of straight stitches 28 and 29. It will be noted that straight stitch 28 passes through panel half 7b, extension web 23 and double fold bias tape 27. Straight stitch 29 additionally passes through that part of extension web 23 folded about the adjacent part of double fold bias tape 27. The raw edge 25 of extension web 23 is finished by a double fold bias tape 30 held thereabout by a straight stitch 31, similar to double fold bias tape 20 and straight stitch 21 of panel half 7a. It will be understood that the extension web 23 runs the full length of slit 18 and when the slit 18 is closed, the extension web 23 is overlapped by the free edge portion of panel half 7a, as is clearly indicated in both FIGS. 1 and 2.

The slit 18 is normally maintained in a closed condition by means of a double coated, water dispersible adhesive tape. Such double coated, water dispersible adhesive tapes are well known in the art. One such tape, for example, is manufactured by Minnesota Mining and Manufacturing Company of St. Paul, Minn. This tape is characterized by the fact that the adhesive on both sides of the backing is water dispersible. Another such tape is manufactured by Plasto S. A. of Chenove, France. This tape is characterized by the fact that the backing, as well as the adhesive coatings on both sides thereof are water dispersible. The term "water dispersible" as used herein and in the claims is to be interpreted sufficiently broadly as to cover both types of tape. The tape is diagrammatically indicated at 32 in FIG. 2 and, like all the other layers is greatly exaggerated in thickness.

The water dispersible tape 32 comes in a roll and is rolled with a release tape. The tape 32 is tacky and is applied to the upper surface (as viewed in FIG. 2) 33 of extension web 23 between double fold bias tapes 27 and 30. The tape 32 adheres to the surface 33. The release paper is removed from the other side of tape 32 and the corresponding part of panel half 7a is pressed against the tape to close slit 18. During steam sterilization or autoclaving, the adhesive coated surfaces of tape 32 become increasingly sticky, firmly joining panel halves 7a and 7b and closing slit 18, thereby maintaining the integrity of the surgical drape at slit 18.

When the surgical procedure is completed, the patient's chest will have certain tubes (and sometimes electrical wires as well) attached thereto through fenestration 12. At this point, the slit 18 is opened by pulling panel halves 7a and 7b apart. This allows the drape 1 to be removed from the patient and around the tubes and wires without destroying the reusable drape or requiring momentary disconnection of the tubes and wires.

In that portion of central panel 7 located between fenestration 12 and the bottom edge 3 of the drape, the panel 7 is provided with a pair of mirror image slits 34 and 35. While the slits 34 and 35 may be rectilinear, it is preferred that they be of angular or "frog-leg" configuration. This is true because the slits 34 and 35 are intended to provide, when open, narrow fenestrations for access to the patient's legs. In a by-pass procedure, for example, this enables removal of veins from the legs, which is normally done from the inside surface of the legs. It is for this reason that the "frog-leg" configuration of slits 34 and 35 is preferred. It will be noted that the slit 34 has, at its ends, short laterally extending portions 36 and 37. The same is, of course, true of slit 35, the short lateral portions being indicated at 38 and 39. This enables the slits 34 and 35 to provide a fenestration when in open condition. This is clearly shown with respect to slit 35 in FIG. 1, the resulting fenestration being indicated at 40.

Since the slits 34 and 35 are mirror images of each other and are otherwise identical, a description of slit 34 can serve as a description of slit 35, as well. It will be understood that the pair of slits 34 and 35 divide the adjacent portions of center panel 7 into a leftmost portion 7c, an intermediate portion 7d, and a rightmost portion 7e, as viewed in FIG. 1.

Reference is also made to FIG. 3 which is a fragmentary, diagrammatic, exploded, cross sectional view taken along section line 3—3 of FIG. 1. Again, as in the case of FIG. 2, all fabric and tape layers are greatly exaggerated in thickness. It will be noted from FIGS. 1 and 3 that the section line 3—3 passes transversely through approximately the longitudinal center of slit 34 at which point both the panel portion 7d and the panel 7c are provided with optional twill tape loops 41 and 42, respectively, which assist in opening the slit 34. The panel portion 7d terminates at slit 34 in a raw edge 43. The twill tape loop 41 terminates in ends 44 and 45 located adjacent raw edge 43. All of these edges are finished by a double fold bias tape 46. The double fold bias tape 46 is attached to the ends of twill tape loop 41 and panel portion 7d by a straight stitch indicated at 48. The twill tape loop 41 is folded about the adjacent portion of the double fold bias tape 46 so as to extend beyond double fold bias tape 46. The loop 41 is maintained in this position by a bartack 49 passing through all of the layers, as is shown in FIG. 3.

The panel portion 7c terminates in a raw edge 50. The twill tape loop 42 terminates in ends 51 and 52 adjacent edge 50. An extension web 53 has a first raw edge 54 and a second raw edge 55. The raw edge 54 is located adjacent and just below raw edge 50 of panel portion 7c, as viewed in FIG. 3. All of ends and edges 50, 51, 52 and 54 are finished by a double fold bias tape 56. The extension web 53 wraps about the adjacent portion of double fold bias tape 56 so as to constitute an extension of panel portion 7c. This entire structure is joined together by a straight stitch 57. In addition, a bartack 58 passes through all of the layers and is essentially coextensive with the width of twill tape loop 42.

It will be apparent from FIG. 3 that the edge portion of panel portion 7d overlaps the extension web 53. The edge portion of panel portion 7d can be affixed to extension web 53 by a layer of double coated, water dispersible adhesive tape 59, which may be substantially identical to double coated, water dispersible adhesive tape 32 of FIG. 2. In a manner similar to that described with respect to FIG. 2, the tape is unwound from a roll and applied to the upper surface (as viewed in FIG. 3) 60 of extension web 53 where it adheres by virtue of its natural tackiness. A release tape (not shown) is removed from the opposite side of tape 59 and the edge portion of panel portion 7d is pressed thereagainst and adhered thereto. Again, the stickiness of both sides of tape 59 increases markedly following steam sterilization or autoclaving. When the slits 34 and 35 are in their closed position such as is shown with respect to slit 34 in FIG. 1, the integrity of the surgical drape 1 in the area of the slits is maintained. By engagement of the loops 41 and 42, the extension web 53 and the edge portion of panel portion 7d can be separated to open the slit 34 to a position similar to that shown with respect to slit 35 in FIG. 1. Once the procedure with respect to the patient's leg has been completed, the slit 34 may be reclosed to reinstate the integrity of the drape 1. It will be understood that the slit 35 is constructed and operates between a closed position and an open position in precisely the same manner.

As indicated above, the cross sectional view of FIG. 3 was taken along section 3—3 of FIG. 1, and includes the loops 41 and 42. It will be understood by one skilled in the art that should the section 3—3 have been located anywhere else along slit 34, FIG. 3 would have been the same with the exception that the loops 41 and 42 would not be present. Neither would the bartacks 49 and 58.

The overlapping elements of slits 18, 34 and 35 have been described as being maintained in a closed condition by a double coated, water dispersible adhesive tape. Other means may be used for this purpose. For example, a water dispersible spray adhesive could be used. A 100% polyester hook and loop tape set could be used. It would even be possible to employ mechanical snaps, although to maintain the integrity of the drape at the slits, the amount of overlap might have to be increased when snaps are used.

At the end of a procedure, the drape will be removed from the patient and washed and dried. The washing step will cause the double coated, water dispersible tape adhesive to dissolve and rinse away during the washing procedure. The entire tape, both adhesive layers and backing strip may dissolve and rinse away, as indicated above. Prior to sterilization, a new strip of double coated, water dispersible adhesive tape will be applied at each slit 18, 34 and 35. As indicated above, when the drape, prior to use, is subjected to steam sterilizing or autoclaving, the holding power of the adhesive tape is enhanced.

It is within the scope of the invention to provide the drape 1 with other appurtenances. For example, it could have an absorbent, textured work area. The drape could further be provided with loop-forming elements having cooperating male and female snap elements whereby they can be formed into closed loops for positioning and guiding tubes, electrical wires and the like, during the procedure. The drape could also be provided with retractor tunnels and flap covers therefore of the type taught in copending application Serial No. 08/120,090, filed Sep. 13, 1993, in the name of Veronica Ann Mills, and entitled SURGICAL DRAPE WITH RETRACTOR TUNNELS. None of the above-noted appurtenances have been illustrated herein, because they do not form a part of the present invention.

An exemplary reusable fabric drape of the type shown in FIG. 1 was made in accordance with the teachings of the present invention and successfully tested. The exemplary reusable drape had an overall width of 86 inches and an overall length of 145 inches. The outer panels 8 and 9 were each made of a single ply of a low liquid repellant fabric such as that manufactured by Standard Textile Co. Inc. of Cincinnati, Ohio under the mark Wrappel™. The central panel 7 of the reusable drape was made of a liquid repellant material. An exemplary material for this purpose is manufactured and sold by Standard Textile Co. Inc. of Cincinnati, Ohio, under the trademark ComPel®R. The extension webs 23 of FIG. 2 and 53 of FIG. 3 were made of the above-noted Wrappel™ material.

In the exemplary drape, the central panel 7 had a width of about 30 inches and the side panels 8 and 9 each had a width of about 28 inches. The fenestration 12 had a head end edge 15 of about 12 inches, side edges 13 and 14 of about 16 inches, and a bottom end edge 16 of about 16 inches. The slit 18 was about 51 inches long and its extension web 23 had a width of about 2 inches. Each of the slits 34 and 35 were about 46 inches long and its respective extension web 53 had a width of about 2 inches.

From the above description, it will be apparent to one skilled in the art that the provision of a slit (like slit 18), extending from the main fenestration 12 to an edge of the drape, would be useful when incorporated in any drape where some sort of tube, wire, or other medical device is attached to the patient at the surgical site through the fenestration. Elongated slits, such as slits 34 and 35, for forming reclosable fenestrations could be applied to any type of reusable surgical drape, where such a slit would be useful.

Modifications may be made in the invention without departing from the spirit of it.

I claim:

1. The fabric reusable surgical drape comprising a cardiovascular drape having peripheral edges, a chest surgical site fenestration, and three elongated slits formed therein, a first one of said elongated slits extending from said chest fenestration to one of said peripheral edges, second and third ones of said elongated slits comprising a mirror image pair and so positioned in said drape as to comprise elongated surgical site fenestrations for access to a patient's legs, each of said three slits having first and second opposed fabric edges, each of said slits having an extension web attached to and along said first fabric edge thereof and extending the length thereof, each of said slits having an open position and a closed position, in said closed position said first and second fabric edges of each slit being substantially abutting with said second edge overlapping said extension web of said first edge, and means to releasably join said second edge thereof and said overlapped extension web thereof together.

2. The fabric reusable surgical drape claimed in claim 1 wherein said binding tape along said first edge of each of said slits also incorporates the adjacent edge of said extension web thereof.

3. The fabric reusable surgical drape claimed in claim 1 wherein said extension webs of said three slits each has a free longitudinal edge, said free edge of each extension web and said first and second edges of each slit being finished with binding tape.

4. The fabric reusable surgical drape claimed in claim 1 wherein each of said second and third slits have short lateral slit extensions at their ends so as to provide a wider fenestration when in said open position.

5. The fabric reusable surgical drape claimed in claim 1 wherein each of said second and third slits comprises two rectilinear angularly related slit portions providing a frog-leg configuration.

6. The fabric reusable surgical drape claimed in claim 1 wherein said means to releasably join together said second edge and said overlapped extension web of each of said first, second and third slits comprises mechanical means.

7. The fabric reusable surgical drape claimed in claim 1 wherein said means to releasably join together said second edge and said extension web of each of said first, second and third slits comprises replaceable water dispersible adhesive means.

8. The fabric reusable surgical drape claimed in claim 7 wherein said replaceable water dispersible adhesive means comprises a tape having an elongated backing web coated both sides with a water dispersible adhesive.

9. The fabric reusable surgical drape claimed in claim 7 wherein said replaceable water dispersible adhesive means comprises a tape having a water dispersible backing web coated both sides with a water dispersible adhesive.

\* \* \* \* \*

UNITED STATES PATENT AND TRADEMARK OFFICE
CERTIFICATE OF CORRECTION

PATENT NO. : 5,515,868
DATED : May 14, 1995
INVENTOR(S) : Veronica Ann Mills

It is certified that error appears in the above-indentified patent and that said Letters Patent is hereby corrected as shown below:

Column 6, line 59 (claim 1), "The" should read --A--.
Column 7, line 9 (claim 2), "1" should read --3--.

Signed and Sealed this

Nineteenth Day of November, 1996

Attest:

BRUCE LEHMAN

Attesting Officer          Commissioner of Patents and Trademarks